(12) United States Patent
Maeda et al.

(10) Patent No.: US 11,065,010 B2
(45) Date of Patent: Jul. 20, 2021

(54) HEMOSTATIC DEVICE

(71) Applicant: TERUMO KABUSHIKI KAISHA, Tokyo (JP)

(72) Inventors: Ryosuke Maeda, Shizuoka (JP); Kenichi Hazama, Bear, DE (US); Junichi Kobayashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 204 days.

(21) Appl. No.: 16/238,258

(22) Filed: Jan. 2, 2019

(65) Prior Publication Data
US 2019/0133604 A1 May 9, 2019

Related U.S. Application Data

(63) Continuation of application No. PCT/JP2017/024385, filed on Jul. 3, 2017.

(30) Foreign Application Priority Data

Jul. 6, 2016 (JP) .............................. JP2016-134598

(51) Int. Cl.
*A61B 17/12* (2006.01)
*A61B 17/135* (2006.01)
(Continued)

(52) U.S. Cl.
CPC ...... *A61B 17/135* (2013.01); *A61B 17/12009* (2013.01); *A61B 17/1325* (2013.01);
(Continued)

(58) Field of Classification Search
CPC ............ A61B 17/135; A61B 17/12009; A61B 17/1325; A61B 17/12; A61B 2017/00637;
(Continued)

(56) References Cited

U.S. PATENT DOCUMENTS

2002/0042585 A1* 4/2002 Kloecker .................. A61F 5/34
602/13
2007/0191881 A1* 8/2007 Amisar .............. A61B 17/1325
606/203
(Continued)

FOREIGN PATENT DOCUMENTS

CN 104703552 A 6/2015
CN 204839640 U 12/2015
(Continued)

OTHER PUBLICATIONS

The extended European Search Report dated Oct. 25, 2019, by the European Patent Office in corresponding European Patent Application No. 17824207.9-1122. (10 pages).
(Continued)

*Primary Examiner* — Erich G Herbermann
(74) *Attorney, Agent, or Firm* — Buchanan Ingersoll & Rooney PC

(57) ABSTRACT

A hemostatic device includes a band for wrapping around a puncture site of a wrist, a mechanism for securing the band to the wrist in a wrapped state, an inflatable portion connected to the band and inflated by being injected with gas, an injection part which is elastically transformable and is capable of injecting air into the inflatable portion, and a tube body that connects an inflatable space of the inflatable portion and a housing space of the injection part to each other, in which the tube body has a hole portion opening in the inflatable portion and a cover portion disposed on the tube body to cover the hole portion, and the cover portion has a communication portion that allows communication between the inflatable space and the housing space by air discharged from the hole portion when air is injected into the inflatable portion from the injection part.

13 Claims, 10 Drawing Sheets

(51) Int. Cl.
   *A61B 17/132* (2006.01)
   *A61B 17/00* (2006.01)

(52) U.S. Cl.
   CPC .............. *A61B 2017/00637* (2013.01); *A61B 2017/12004* (2013.01); *A61B 2017/12018* (2013.01); *A61L 2400/04* (2013.01)

(58) Field of Classification Search
   CPC A61B 2017/12004; A61B 2017/12018; A61B 5/02233; A61L 2400/04; A61F 5/30
   See application file for complete search history.

(56) References Cited

U.S. PATENT DOCUMENTS

| | | | |
|---|---|---|---|
| 2010/0010404 A1 | 1/2010 | Nardi et al. | |
| 2014/0171734 A1* | 6/2014 | Kassman | A61H 19/40 600/38 |
| 2015/0032149 A1 | 1/2015 | Croushom et al. | |
| 2015/0201948 A1 | 7/2015 | Kornowski et al. | |

FOREIGN PATENT DOCUMENTS

| | | |
|---|---|---|
| CN | 105682577 A | 6/2016 |
| CN | 108882943 A | 11/2018 |
| EP | 2 677 945 B1 | 11/2014 |
| EP | 3 434 205 A1 | 1/2019 |
| GB | 2504778 A | 2/2014 |
| JP | 18-003029 Y1 | 3/1943 |
| JP | 3031486 U | 11/1996 |
| JP | 2007054123 A | 3/2007 |
| WO | 98/46144 A1 | 10/1998 |

OTHER PUBLICATIONS

International Search Report (PCT/ISA/210) dated Oct. 10, 2017, by the Japan Patent Office as the International Searching Authority for International Application No. PCT/JP2017/024385.

Written Opinion (PCT/ISA/237) dated Oct. 10, 2017, by the Japan Patent Office as the International Searching Authority for International Application No. PCT/JP2017/024385.

An English Translation of the International Search Report (Form PCT/ISA/210) and the Written Opinion of the International Searching Authority (Form PCT/ISA/237) dated Oct. 10, 2017, by the Japanese Patent Office in corresponding International Application No. PCT/JP2017/024385. (5 pages).

Office Action (Notification of the First Office Action) dated Dec. 1, 2020, by the National Intellectual Property Administration, PRC in corresponding Chinese Patent Application No. 201780041753.9 and an English Translation of the Office Action. (16 pages).

* cited by examiner

HEMOSTATIC DEVICE

CROSS-REFERENCE TO RELATED APPLICATIONS

This application is a continuation of International Application No. PCT/JP2017/024385, filed on Jul. 3, 2017, which claims priority to Japanese Patent Application No. 2016-134598, filed on Jul. 16, 2016, the entire content of both being incorporated herein by reference.

TECHNICAL FIELD

The present invention relates to a hemostatic device for performing hemostasis by pressing a punctured site.

BACKGROUND DISCUSSION

Recently, percutaneous treatment/examination, etc. has been performed by puncturing a blood vessel of an arm, a leg, etc., introducing an introducer sheath to a puncture site, and delivering a medical instrument such as a catheter to a lesion through a lumen of the introducer sheath. When such treatment/examination, etc. is performed, an operator needs to perform hemostasis in the puncture site after withdrawing the introducer sheath. To perform hemostasis, there has been a known hemostatic device including a band for wrapping around a limb such as an arm, a leg, etc., means for securing that secures the band in a state of being wrapping around the limb, and an inflatable portion connected to the band to press the puncture site by inflating in response to injection of a fluid.

As described in Japanese Utility Model Application No. 7-7965, when a hemostatic device is used, in general, a doctor or a nurse connects a dedicated instrument such as a syringe separate from the hemostatic device to a port communicating with an inflatable portion of the hemostatic device and injects a fluid into the inflatable portion using the dedicated instrument, thereby inflating the inflatable portion of the hemostatic device.

When the dedicated instrument separate from the hemostatic device is used as described above, it takes an effort to carry the dedicated instrument and an effort to connect the dedicated instrument to the hemostatic device. In addition, when the dedicated instrument is lost, there is a possibility of occurrence of a situation in which a fluid may not be injected into the inflatable portion.

To solve the above-mentioned problem, there is a need for a hemostatic device capable of inflating an inflatable portion by a simple operation without using a dedicated instrument separate from the hemostatic device.

SUMMARY

A hemostatic device according to an exemplary embodiment of the disclosure herein includes a band for wrapping around a site of a limb where bleeding is to be stopped, means for securing that secures the band to the limb in a wrapped state, an inflatable portion connected to the band and inflated by being injected with gas, an injection part which is elastically transformable and is capable of injecting gas into the inflatable portion, and a tube body that connects a lumen of the inflatable portion and a lumen of the injection part to each other, wherein the tube body has a hole portion opening in the inflatable portion and a cover portion disposed on the tube body to cover the hole portion, and the cover portion has a communication portion that allows communication between the lumen of the inflatable portion and the lumen of the injection part by gas discharged from the hole portion when gas is injected into the inflatable portion from the injection part.

In the hemostatic device of the exemplary embodiment, when the injection part is elastically transformed, gas moves through a lumen of the tube body. The communication portion of the cover portion allows communication between the lumen of the inflatable portion and the lumen of the injection part by movement of gas. The inflatable portion inflates by being injected with gas via the communication portion. In addition, by the lumen of the tube body becoming negative pressure with respect to the inflatable space of the inflatable portion when the injection part is elastically transformed to return to an original shape, the communication portion blocks communication between the lumen of the inflatable portion and the lumen of the injection part. In this way, the hemostatic device can easily and appropriately control movement of gas between the inflatable portion and the injection part by the communication portion formed in the cover portion. Therefore, according to the disclosure, it is possible to provide the hemostatic device capable of inflating the inflatable portion by a simple operation without using a dedicated instrument separate from the hemostatic device.

DETAILED DESCRIPTION

Figure 1:
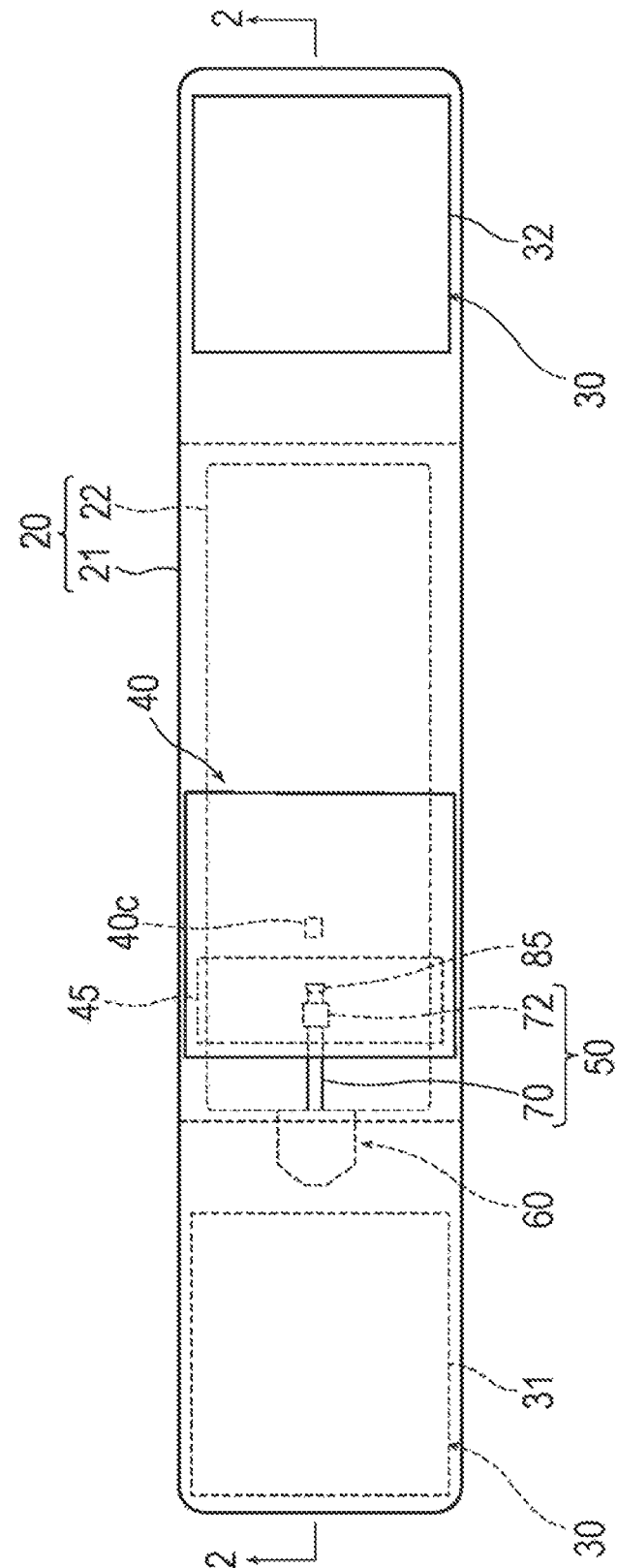
FIG. 1 is a plan view of a hemostatic device according to an embodiment viewed from an inner surface side.

Hereinafter, an exemplary embodiment of the disclosure and modifications thereof will be described with reference to accompanying drawings. Note that a description below does not restrict a technical scope or a meaning of a term described in the claims. In addition, a ratio of dimensions in the drawings is exaggerated for convenience of description and may be different from an actual ratio.

Figure 6:
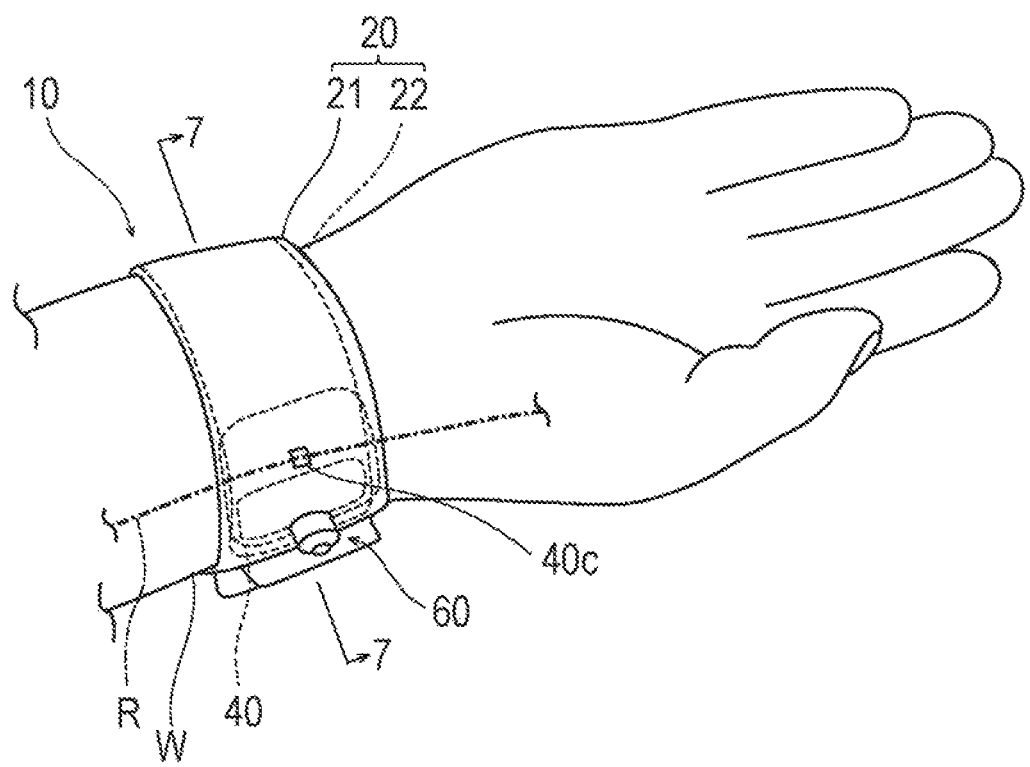
FIG. 6 is a perspective view illustrating a state in which the hemostatic device according to the embodiment is mounted on a wrist.
Figure 7:
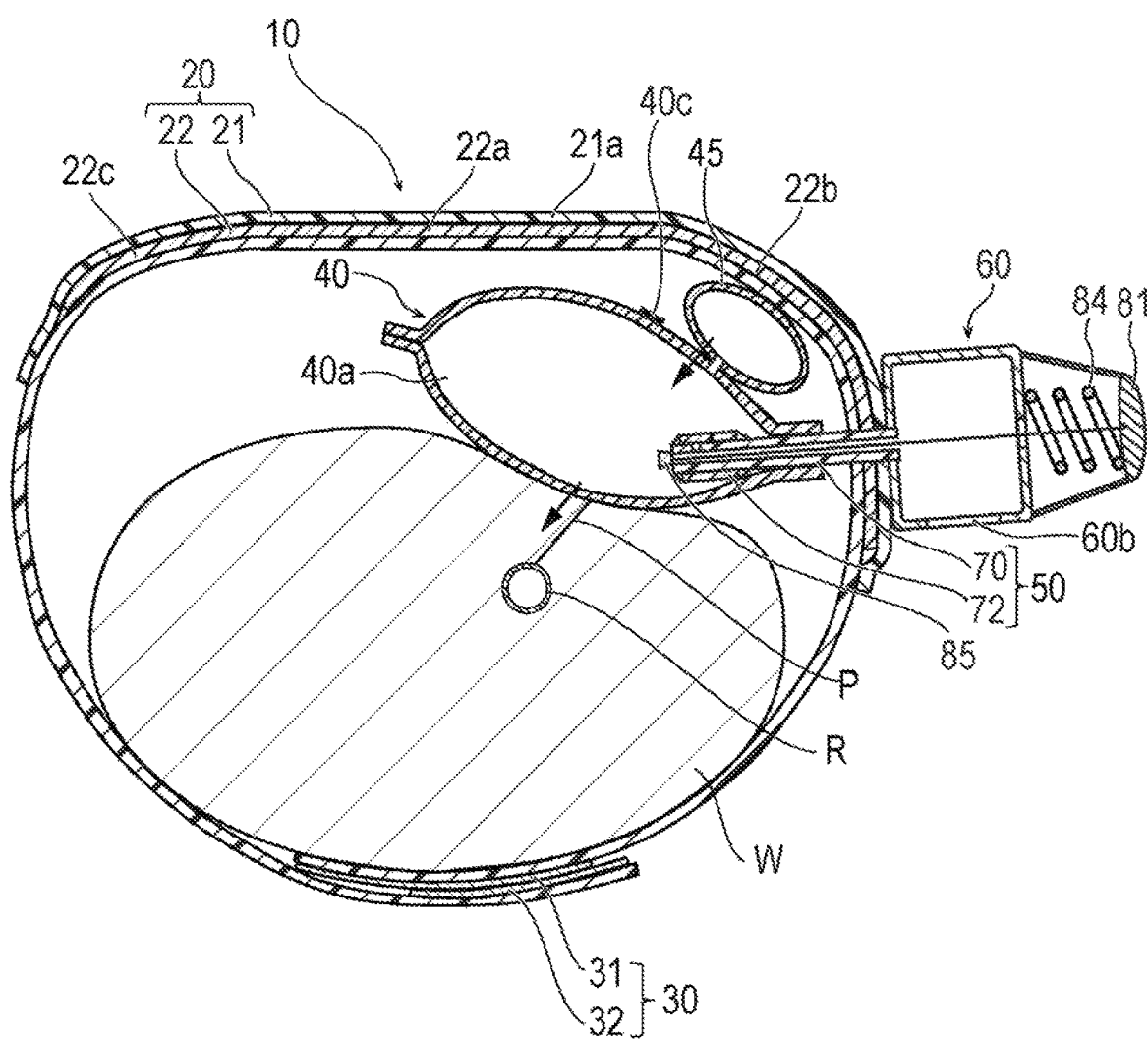
FIG. 7 is a cross-sectional view taken along 7-7 line of FIG. 6.

A hemostatic device 10 according to the exemplary embodiment will be described with reference to FIG. 1 to FIG. 7. FIG. 1 to FIG. 5(B) are diagrams for description of each portion of the hemostatic device 10. FIG. 6 and FIG. 7 are diagrams for description of the hemostatic device 10 in use.

As illustrated in FIG. 6 and FIG. 7, to insert a catheter, etc. for performing treatment/examination, etc. into a blood vessel, after withdrawing an introducer sheath indwelled in a puncture site P (corresponding to a "site where bleeding is to be stopped") formed in a radial artery R of a wrist W (corresponding to a "limb"), the hemostatic device 10 according to the embodiment is used to stop bleeding in the puncture site P.

Figure 2:
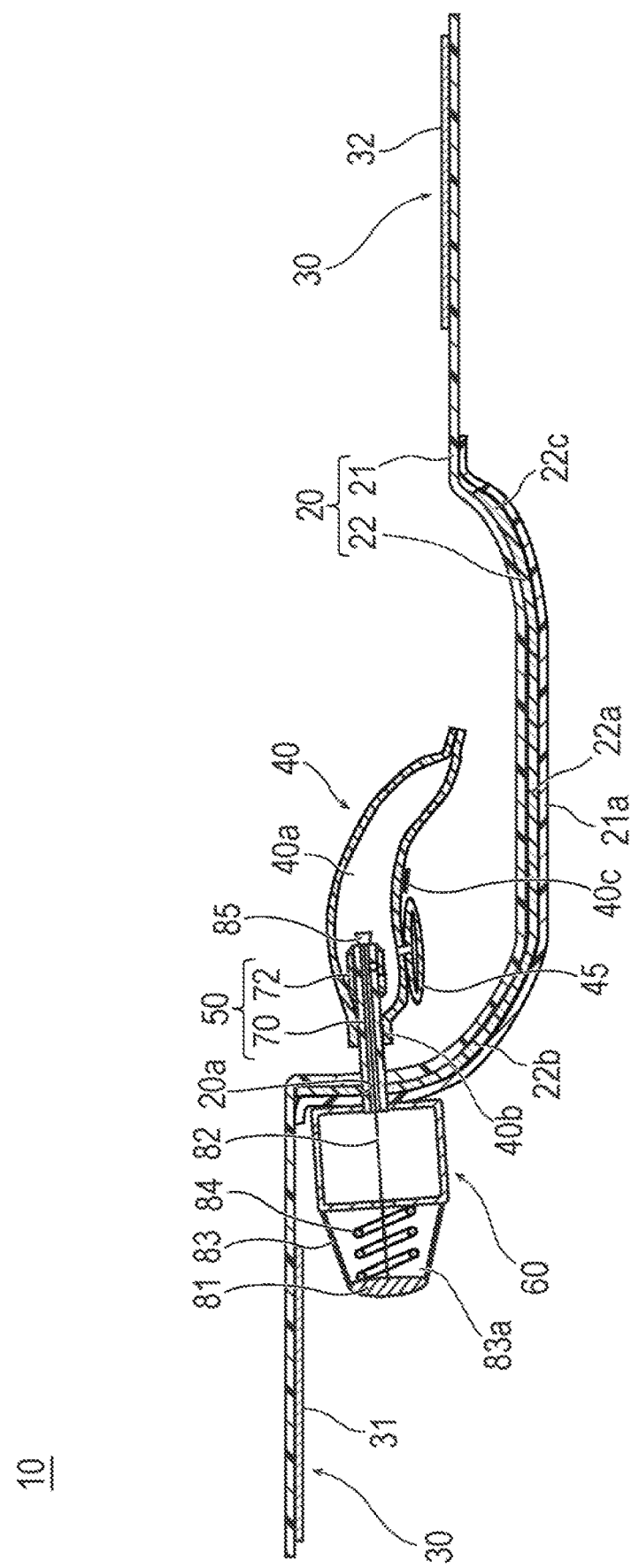
FIG. 2 is a cross-sectional view taken along 2-2 line of FIG. 1.

As illustrated in FIG. 1 and FIG. 2, the hemostatic device 10 includes a band 20 for wrapping around the wrist W, a surface fastener 30 (corresponding to "means for securing (securing member)") that secures the band 20 in a state of being wrapped around the wrist W, an inflatable portion 40 that inflates by being injected with air (corresponding to "gas") and presses the puncture site P, an auxiliary pressing portion 45 provided between the inflatable portion 40 and the band 20, a marker 40c for positioning the inflatable portion 40 at the puncture site P, an injection part 60 capable of injecting air into the inflatable portion 40 and the auxiliary pressing portion 45, and a tube body 70 that connects an inflatable space 40a (lumen) of the inflatable portion 40 to a housing space 60a (lumen) of the injection part 60.

In the disclosure herein, when the band 20 is wrapped around the wrist W, a surface (mounting surface) on a side facing a body surface of the wrist W is referred to as an "inner surface", and a surface on an opposite side is referred to as an "outer surface".

The band 20 includes a belt 21 made of a belt-shaped member having flexibility and a support plate 22 having a higher hardness than that of the belt 21.

As illustrated in FIG. 6 and FIG. 7, the belt 21 is wrapped around an outer periphery of the wrist W substantially once. As illustrated in FIG. 2, a support plate holding portion 21a that holds the support plate 22 is formed at a central portion of the belt 21. The support plate holding portion 21a is doubled by separate belt-shaped members joined to an outer surface side (or inner surface side) using a method such as welding (heat-welding, high-frequency welding, ultrasound welding, etc.) or adhesion (adhesion by an adhesive or a solvent) and holds the support plate 22 inserted into a gap therebetween.

A male side (or a female side) 31 of the surface fastener 30 is disposed on an outer surface side of a portion of the belt 21 near a left end as illustrated in FIG. 1, and a female side (or a male side) 32 of the surface fastener 30 is disposed on an inner surface side of a portion of the belt 21 near a right end as illustrated in FIG. 1. For example, the surface fastener 30 is a hook and loop fastener known as a general product such as VELCRO (registered trademark) or Magic tape (registered trademark) in Japan. As illustrated in FIG. 7, the belt 21 is wrapped around the wrist W, and the male side 31 and the female side 32 are joined together, thereby mounting the band 20 on the wrist W. Note that means for securing the band 20 to the wrist W in a wrapped state is not limited to the surface fastener 30. For example, the means may correspond to a securing member such as a snap, a button, a clip, or a frame member passing an end portion of the belt 21.

The constituent material of the belt 21 is not particularly limited as long as the material has flexibility. Examples of such a material include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

In addition, at least a part of the belt 21 overlapping with the inflatable portion 40 is preferably substantially transparent. However, the part may not be transparent, and may be translucent or colored transparent. In this way, the puncture site P may be visually recognized from the outer surface side, and the marker 40c described below may be easily positioned at the puncture site P.

As illustrated in FIG. 2, the support plate 22 is held in the belt 21 by being inserted into the doubly formed support plate holding portion 21a of the belt 21. At least a part of the support plate 22 has a plate shape curved toward the inner surface side (mounting surface side). The support plate 22 is made of a harder material than that of the belt 21 and is designed to maintain a substantially constant shape. However, a method of disposing the support plate 22 on the belt 21 is not limited to an illustrated configuration, and it is possible to include joining the support plate 22 to the inner surface or the outer surface of the band 20 using an appropriate method such as welding or adhesion. Similarly, another acceptable configuration is a configuration in which the belt 21 is connected to both end portions of the support plate 22. For this reason, it is not always necessary that the entire support plate 22 overlaps the belt 21.

The support plate 22 has a shape elongated in a longitudinal direction of the belt 21. A central portion 22a in a longitudinal direction of the support plate 22 is formed in a flat plate shape with little curvature. A first curved portion 22b (left side of FIG. 2) and a second curved portion 22c (right side of FIG. 2) curved toward an inner circumference side and along the longitudinal direction of the belt 21 (circumferential direction of the wrist W) are formed on both sides of the central portion 22a, respectively.

Examples of the constituent material of the support plate 22 include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

It is preferable that a part of the support plate 22 overlapping the inflatable portion 40 is substantially transparent similar to the belt 21. However, the part of the support plate 22 may not be transparent, and may be translucent or colored transparent. In this way, the puncture site P may be reliably visually recognized from the outer surface side, and the marker 40c described below may be easily positioned at the puncture site P. Note that the support plate 22 may not be a plate having a non-curved portion as the central portion 22a, that is, it may be a plate having a curvature over an entire length thereof.

The inflatable portion 40 has a function of inflating by being injected with air to apply a pressing force to the puncture site P. In the exemplary embodiment, as illustrated in FIG. 1 and FIG. 2, the inflatable portion 40 is formed of a bag-shaped member obtained by superimposing two substantially rectangular sheets and bonding or welding a circumference thereof. In this way, the inflatable space 40a is formed between the two sheets. Note that a configuration of the inflatable portion 40 is not particularly limited as long as the inflatable portion 40 can be inflated by being injected with air. For example, the inflatable portion 40 may be formed of a bag-shaped member obtained by folding one sheet and bonding or welding edge portions, or formed of a balloon-shaped member not having an edge portion. In addition, an external shape of the inflatable portion 40 is not particularly limited. For example, the inflatable portion 40 may have an external shape such as a circle, an ellipse, or a polygon in plan view in a non-inflated state.

As illustrated in FIG. 2, the inflatable portion 40 is disposed to overlap a vicinity of a portion between the first curved portion 22b and the central portion 22a of the support plate 22. For this reason, as illustrated in FIG. 7, when the inflatable portion 40 is inflated, inflation of the inflatable portion 40 in a direction away from the body surface of the wrist W is suppressed by the belt 21 and the support plate 22, and a pressing force of the inflatable portion 40 is concentrated on the wrist W side. Thus, it is possible to suitably press the puncture site P.

The inflatable portion 40 has a connecting portion 40b connected to the tube body 70. The inflatable portion 40 is connected to the tube body 70 through the connecting portion 40b in a state in which a part of the tube body 70 is inserted into the inflatable space 40a. The tube body 70 is connected to the band 20 in a state of penetrating a through-hole 20a formed in the band 20. A method of connecting the inflatable portion 40 to the tube body 70 and a method of connecting the tube body 70 to the band 20 are not particularly limited. For example, it is possible to adopt a method such as welding or adhesion using an adhesive. Also, the inflatable portion 40 may be directly connected to the belt 21 of the band 20. In addition, the tube body 70 may be secured to an arbitrary member amongst the belt 21 of the band 20, the support plate 22 of the band 20, and the injection part 60.

The constituent material of the inflatable portion 40 is not particularly limited as long as the material has flexibility. For example, it is possible to use the same material as the constituent material of the band 20 described above.

It is preferable that the inflatable portion 40 is substantially transparent. However, the inflatable portion 40 may not be transparent, and may be translucent or colored transparent. In this way, the puncture site P may be visually recognized from the outer surface side, and the marker 40c described below may be easily positioned at the puncture site P.

As indicated by an arrow in FIG. 7, the auxiliary pressing portion 45 has a function of pressing the inflatable portion 40 to adjust a direction of a pressing force applied to the puncture site P by the inflatable portion 40.

Similar to the inflatable portion 40, the auxiliary pressing portion 45 is formed of a bag-shaped member. Note that for example, the auxiliary pressing portion 45 may be made of a sponge-like substance, an elastic material, an aggregate of fibers such as cotton, a combination thereof, etc.

The auxiliary pressing portion 45 is attached to the inflatable portion 40 such that an internal space thereof communicates with the inflatable space 40a of the inflatable portion 40. For this reason, when air is injected into the inflatable portion 40, the auxiliary pressing portion 45 is also inflated.

As illustrated in FIG. 2, the marker 40c is provided at an approximate center of the inflatable portion 40 on a side facing the band 20. When such a marker 40c is provided on the inflatable portion 40, the inflatable portion 40 can be easily positioned with respect to the puncture site P, and thus position shift of the inflatable portion 40 is suppressed. Note that the marker 40c may be provided on a side of the inflatable portion 40 facing the wrist W. In this instance, it is preferable that the marker 40c is provided on the inner surface of the inflatable portion 40 so as not to directly come into contact with the puncture site P. Note that a position at which the marker 40c is provided is not particularly limited as long as the inflatable portion 40 can be positioned at the puncture site P. For example, the marker 40c may be provided on the belt 21 or the support plate 22 as long as the inflatable portion 40 can be positioned at the puncture site P.

The shape of the marker 40c is not particularly limited, and examples thereof include a circle, a triangle, a quadrangle, etc. In present embodiment, the shape corresponds to the quadrangle.

The size of the marker 40c is not particularly limited. For example, when the shape of the marker 40c corresponds to the quadrangle, it is preferable that a length of one side thereof is in a range of 1 to 4 mm. When the length of the one side is 5 mm or more, the size of the marker 40c increases with respect to a size of the puncture site P, and thus it is difficult to position a central portion of the inflatable portion 40 at the puncture site P.

The material of the marker 40c is not particularly limited. Examples thereof include an oily coloring agent such as ink, a resin kneaded with a pigment, etc.

The color of the marker 40c is not particularly limited when the color allows the inflatable portion 40 to be positioned at the puncture site P. However, a green-based color is preferable. When the green-based color is adopted, it is easy to visually recognize the marker 40c on blood or skin, and thus the inflatable portion 40 is more easily positioned at the puncture site P.

In addition, the marker 40c is preferably translucent or colored transparent. In this way, the puncture site P may be visually recognized from the outer surface side of the marker 40c.

A method of providing the marker 40c on the inflatable portion 40 is not particularly limited. Examples thereof include a process of printing the marker 40c on the inflatable portion 40, a method of welding the marker 40c to the inflatable portion 40, a method of applying an adhesive to one surface of the marker 40c to paste the marker 40c to the inflatable portion 40, etc.

Figure 3:
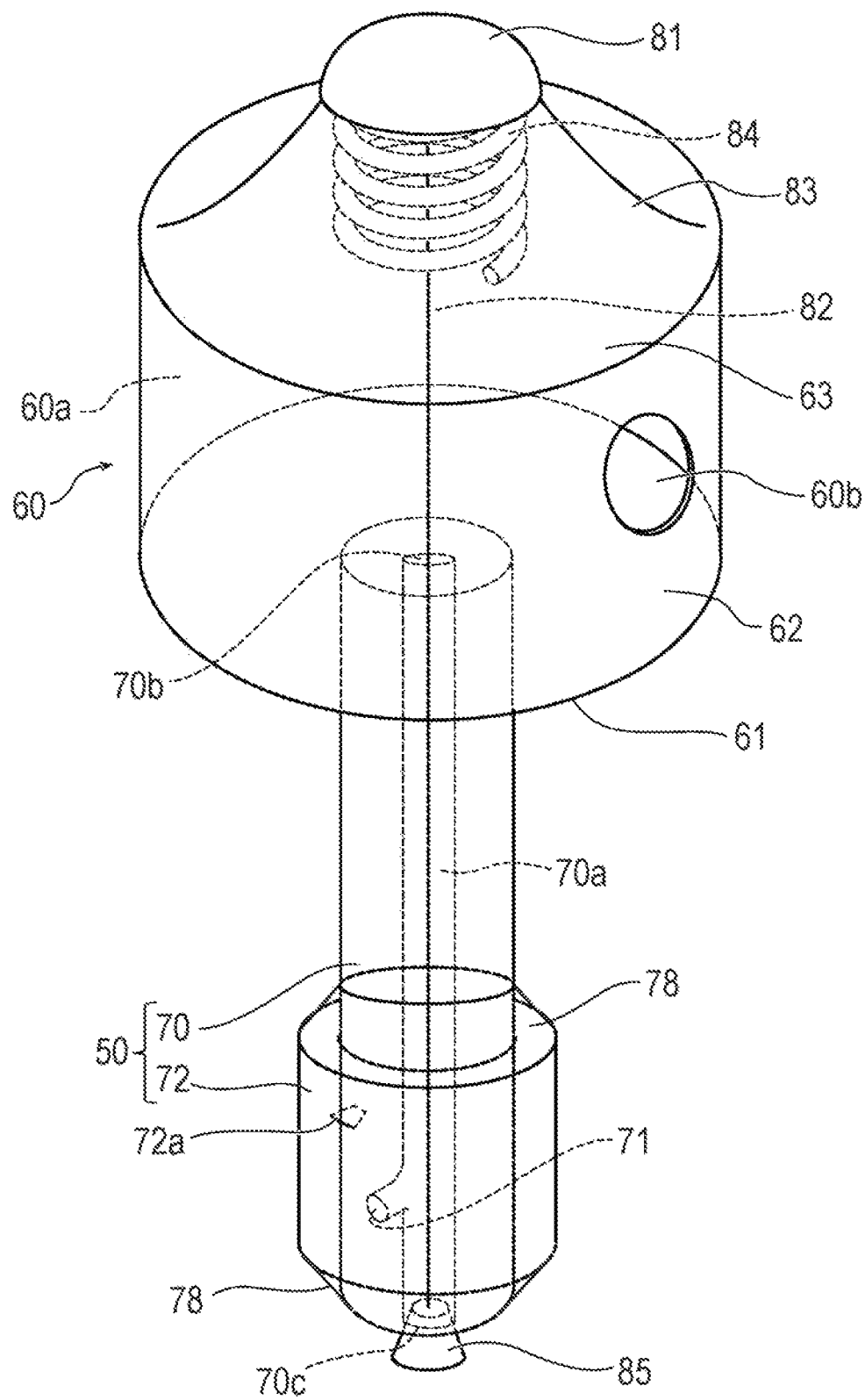
FIG. 3 is a schematic perspective view of an injection part and a tube body included in the hemostatic device according to the embodiment.

Next, a description will be given of the injection part 60 and the tube body 70. FIG. 3 illustrates a schematic perspective view of the injection part 60 and the tube body 70.

The injection part 60 has a function of injecting air into the inflatable portion 40. The tube body 70 has a cover portion 72 attached to the tube body 70. The tube body 70 and the cover portion 72 are included in a backflow check structure 50 that prevents air from being inadvertently discharged from the inflatable space 40a of the inflatable portion 40.

As illustrated in FIG. 2 and FIG. 3, the injection part 60 is configured by a three-dimensional (3D) member including a housing space (lumen) 60a capable of housing air.

The injection part 60 includes a bottom face part 61 disposed on the outer surface side of the band 20, a vertical wall part 62 projecting from the bottom face part 61 to a side at which the band 20 is not provided, and an upper face part 63 which is continued from the vertical wall part 62 and faces the bottom face part 61. A hole portion 60b communicating between an inside and an outside of the housing space 60a is formed in the vertical wall part 62.

The housing space 60a corresponds to a space surrounded by the bottom face part 61, the vertical wall part 62, and the upper face part 63. In the exemplary embodiment, the injection part 60 is formed to have a columnar external shape. However, the external shape of the injection part 60 is not particularly limited. For example, the external shape of the injection part 60 may correspond to a polygonal prism such as a quadrangular prism, a sphere having no distinction between the bottom face part, the vertical wall part, and the upper face part, etc. In addition, for example, the injection part 60 may be formed in a tapered shape in which an outer circumference of the vertical wall part 62 decreases from the bottom face part 61 side toward the upper face part 63 side (direction away from the bottom face part 61) (a shape in which the outer circumference gradually decreases from the bottom face part 61 toward the upper face part 63 side in a cross section illustrated in FIG. 4(A)).

The volume of the housing space 60a of the injection part 60 is preferably about ¼ to ⅓ of the volume of the inflatable space 40a of the inflatable portion 40. In this way, the injection part 60 is formed to an appropriate size to prevent the injection part 60 from hindering manipulation, etc. performed around the hemostatic device 10, and it is possible to reduce the number of times of performing an injection operation of injecting air into the inflatable portion 40 described below.

The injection part 60 is disposed on the outer surface side of the band 20. For this reason, when compared to a case in which the injection part 60 is provided to protrude from the band 20 to the wrist W side, the injection part 60 rarely comes into contact with the wrist W of the wearer, and thus it is possible to reduce discomfort felt by the wearer. In addition, since the injection operation of injecting air into the inflatable portion 40 is performed on the support plate 22 having the high hardness, the injection operation is facilitated. Note that a position at which the injection part 60 is disposed is preferably disposed on the band 20. However, the position is not particularly limited.

The hole portion 60b formed in the injection part 60 penetrates the vertical wall part 62 in a direction intersecting with an extending direction of the injection part 60 (vertical direction of FIG. 3). The hole portion 60b allows air to be taken into the housing space 60a. For example, when the inflatable portion 40 is inflated, as illustrated in FIG. 4(B), a finger is placed to grip the injection part 60, and the injection part 60 is deformed while the hole portion 60b is blocked with the finger. By this operation, air in the housing space 60a is sent to a lumen 70a of the tube body 70 connected to the injection part 60. As described below, the air sent to the lumen 70a of the tube body 70 allows communication between the lumen 70a of the tube body 70 and the inflatable space 40a of the inflatable portion 40.

As described above, the hole portion 60b of the injection part 60 is formed in the vertical wall part 62. For this reason, a pressing force at the time of deforming the injection part 60 on the vertical wall part 62C, becomes relatively difficult to be transmitted to the puncture site P positioned on the inner surface side of the band 20 (see FIG. 7). Therefore, it is possible to suitably prevent a situation in which the puncture site P is unnecessarily pressed by an injection operation of injecting air into the inflatable portion 40. In addition, as described above, since the pressing force for deforming the injection part 60 becomes relatively difficult to be transmitted to the puncture site P, when the inflatable portion 40 is inflated, the wearer can relatively accurately detect only a pressing force applied to the puncture site P by the inflatable portion 40. In this way, it is possible to inject an optimum amount of air for hemostasis of the puncture site P into the inflatable portion 40 based on a pressing force felt by the wearer. Further, since the hole portion 60b is formed in the vertical wall part 62, when compared to a case in which the hole portion 60b is formed in the upper face part 63, a possibility that the hole portion 60b will come into contact with a surrounding article, etc. and be blocked decreases. For this reason, it is possible to prevent the injection part 60 from being unintentionally deformed to inadvertently inject air into the inflatable portion 40.

Note that the number of hole portions 60b formed in the injection part 60, a position and a shape of the hole portion 60b, etc. are not particularly limited and may be appropriately changed as long as air can be injected into the inflatable portion 40 from the injection part 60.

For example, the injection part 60 may be made of an elastomer material such as silicone rubber or latex rubber, a thermoplastic plastic material such as polypropylene or polyethylene, or various thermoplastic elastomer materials having both properties of these materials.

Figure 4A:
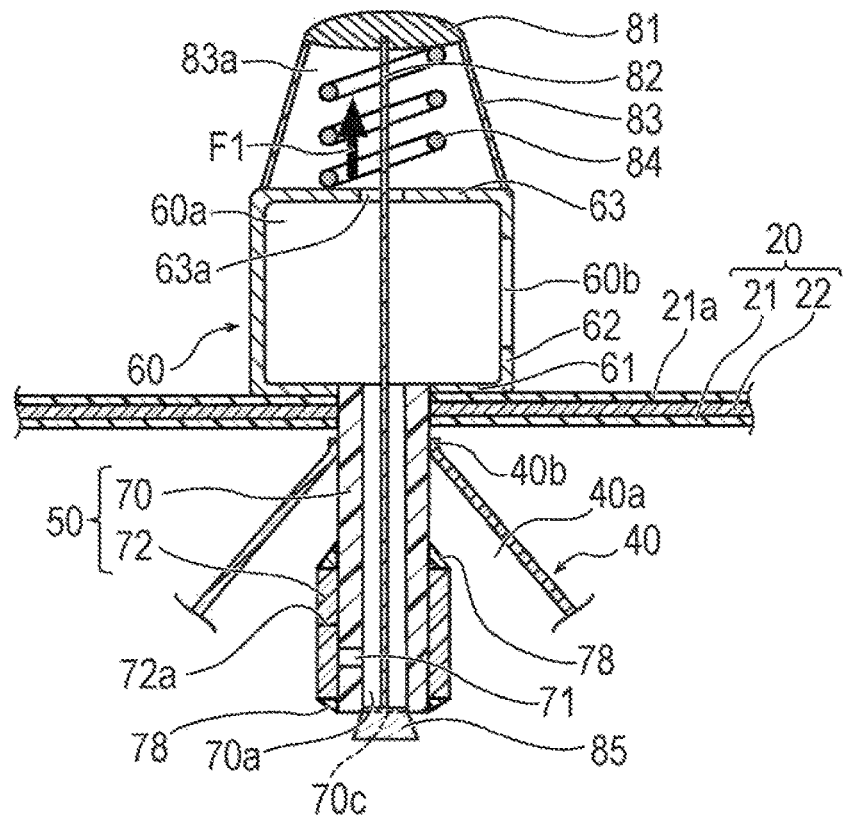
FIG. 4(A) is a cross-sectional view illustrating a state in which a lumen of the inflatable portion and a lumen of the tube body do not communicate with each other.
Figure 4B:
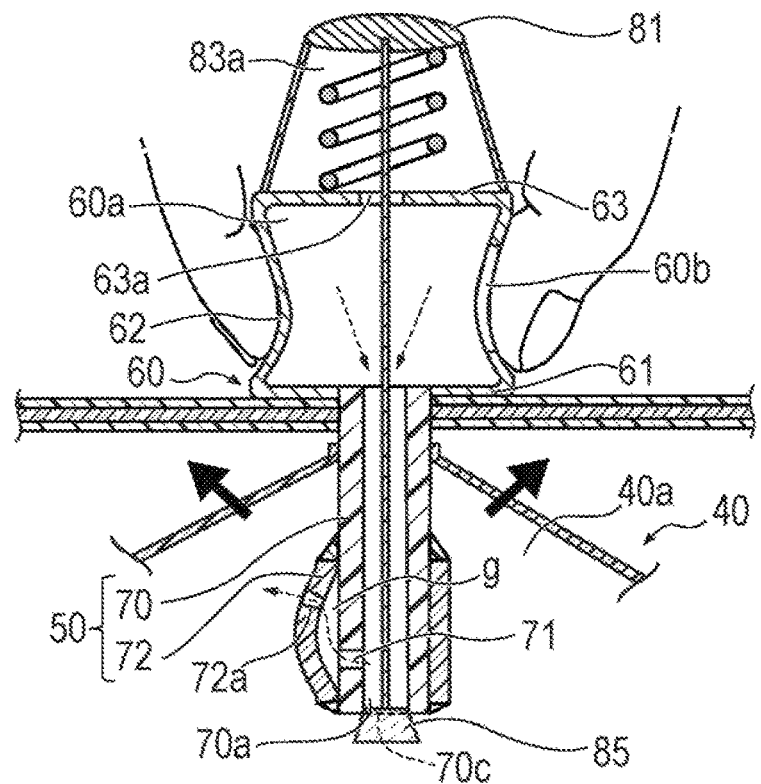
FIG. 4(B) is a cross-sectional view illustrating a state when gas is moving from the injection part to the inflatable portion.

As illustrated in FIG. 3 and FIG. 4(A), the tube body 70 is attached to the bottom face part 61 side of the injection part 60. The tube body 70 has the lumen 70a through which air can flow, a proximal end opening 70b which communicates with the lumen 70a and is disposed to face the housing space 60a of the injection part 60, a distal end opening 70c disposed inside the inflatable space 40a of the inflatable portion 40, and a hole portion 71 opening in the inflatable portion 40.

The tube body 70 further has the cover portion 72 disposed on the tube body 70 to cover the hole portion 71. The cover portion 72 has a communication portion 72a capable of switching between communication between the lumen 70a of the tube body 70 and the inflatable space 40a of the inflatable portion 40 and blocking of a communication state.

The tube body 70 has a substantially columnar external shape. The lumen 70a of the tube body 70 is formed along an extending direction (axial direction) of the tube body 70. The hole portion 71 of the tube body 70 is formed on a distal side of the tube body 70 (lower side of FIG. 3), and opens toward an outer surface of the tube body 70 so as to be orthogonal to the lumen 70a of the tube body 70.

The cover portion 72 is formed in a substantially cylindrical shape, and is disposed to cover the distal side of the tube body 70. An inner diameter of the cover portion 72 is formed to have a size at which the cover portion 72 is in close contact with the outer surface of the tube body 70 in a state in which the cover portion 72 is disposed on the tube body 70 to cover the hole portion 71. For this reason, in a state in which air is not injected into the inflatable portion 40 from the injection part 60 (see FIG. 4(A)), the outer surface of the tube body 70 and an inner surface of the cover portion 72 are in close contact with each other.

A constituent material of the tube body 70 preferably corresponds to a material having higher hardness than that of the cover portion 72. Examples of such a material include a known metallic material, a plastic material, etc.

A constituent material of the cover portion 72 preferably corresponds to an elastic member. Examples of such a material include an elastomer material such as butyl rubber, polysulfide rubber, epichlorohydrin rubber, high nitrile rubber, fluororubber, or silicone rubber, various thermoplastic elastomer materials, etc.

As illustrated in FIG. 4(A), a distal portion and a proximal portion of the cover portion 72 are secured to the tube body 70 in a state in which a space between the portions and the outer surface of the tube body 70 is sealed. The cover portion 72 and the tube body 70 are secured by an adhesive 78. However, securing may be performed by welding. When the space between the distal portion and the proximal portion of the cover portion 72 and the outer surface of the tube body 70 is sealed, it is possible to prevent air from being released from a distal side and a proximal side of the cover portion 72. In this way, air passing through the lumen 70a of the tube body 70 is efficiently sent to the communication portion 72a, and thus it is possible to move air into the inflatable space 40a via the communication portion 72a. Note that if air is released from the distal side and the proximal side of the cover portion 72, the distal portion and the proximal portion of the cover portion 72 may not be secured to the outer surface of the tube body 70.

In the exemplary embodiment, the communication portion 72a of the cover portion 72 is formed as a slit (cut) penetrating the cover portion 72 in a thickness direction. The slit is formed on the proximal side of the hole portion 71 of the tube body 70 (upper side of FIG. 4(A)) so as not to overlap with the hole portion 71 of the tube body 70 in a cross section perpendicular to an axial center of the tube body 70 (cross section illustrated in FIG. 4(A)). In addition, one slit is formed in the cover portion 72 in a shape extending in a direction orthogonal to an extending direction (axial direction) of the cover portion 72.

As described above, for example, the communication portion 72a may be formed as the slit. However, as described below, the communication portion 72a is not limited to a form of the slit as long as it is possible to switch between communication between the inflatable space 40a of the inflatable portion 40 and the lumen 70a of the tube body 70 and blocking of the communication state. For example, the communication portion 72a may be formed as a small hole having the same function as that of the slit. In addition, for example, the communication portion 72a may be formed as a plurality of slits, formed as a slit having a shape extending in a direction inclined with respect to the extending direction of the cover portion 72, or formed as a plurality of slits intersecting and overlapping each other. A specific shape, structure, arrangement, etc. are not particularly limited. In addition, in a case in which the communication portion 72a is formed as the small hole, a specific shape, size, structure, arrangement, etc. are not similarly particularly limited, and it is possible to adopt the above exemplified configuration, etc.

In the exemplary embodiment, the hole portion 71 included in the tube body 70 is formed in a circular shape in plan view. However, the shape of the hole portion 71 is not particularly limited as long as air can flow, and may correspond to, for example, a rectangular shape, an elliptical shape, a trapezoidal shape, another polygonal shape, etc. in plan view.

As illustrated in FIG. 3 and FIG. 4(B), the injection part 60 has an operation portion 81 disposed on the outer surface of the injection part 60 and an occlusion member 85 connected to the operation portion 81.

The operation portion 81 is disposed on the upper face part 63 side of the injection part 60. The operation portion 81 is connected to the occlusion member 85 by an insertion member 82 inserted into a through-hole 63a formed in the upper face part 63 of the injection part 60 and the lumen 70a of the tube body 70. When the operation portion 81 is pressed to approach the injection part 60, the occlusion member 85 connected to the operation portion 81 moves to the distal side of the tube body 70 in conjunction with the operation portion 81.

For example, a hard resin material or a metallic material may be used as a material forming the insertion member 82.

The operation portion 81 has an urging member 84 disposed on the upper face part 63 of the injection part 60.

In a state in which the operation portion 81 is not pressed, the occlusion member 85 seals the distal end opening 70c of the tube body 70 (see FIG. 4(A)). In addition, the urging member 84 applies an urging force (arrow F1 of FIG. 4(A)) for pressing the occlusion member 85 against the distal end opening 70c so that a state in which the occlusion member 85 seals the distal end opening 70c can be maintained. Specifically, the operation portion 81 is pushed upward by a pulling force applied by the urging member 84 in a direction away from the upper face part 63 of the injection part 60 to butt the occlusion member 85 against the distal end opening 70c of the tube body 70. When the operation portion 81 is pressed and the occlusion member 85 moves to the distal side of the tube body 70 against the urging force of the urging member 84, the distal end opening 70c is in a state of communicating with the inflatable space 40a of the inflatable portion 40.

The urging member 84 includes a spring (coil spring) that can be compressed in an extending direction of the tube body 70. However, the urging member 84 is not particularly limited as long as the urging member 84 can apply an urging force in a pulling direction with respect to the occlusion member 85. For example, the urging member 84 may include a leaf spring, a torsion spring, an elastic member capable of applying an elastic force associated with compression and extension, etc.

The occlusion member 85 is formed in a truncated conical cross-sectional shape in which an outer diameter of the proximal side positioned on the distal end opening 70c side is smaller than an outer diameter on the distal side. When the occlusion member 85 is formed in such a cross-sectional shape, the proximal portion is in close contact with and fits into the distal end opening 70c, and thus airtightness of the distal end opening 70c is improved. Note that the cross-sectional shape of the occlusion member 85 is not particularly limited as long as the distal end opening 70c of the tube body 70 can be sealed (occluded). For example, the cross-sectional shape may correspond to a spherical shape, a columnar shape, etc.

For example, a material forming the occlusion member 85 may be the same material as that of the cover portion 72.

As illustrated in FIG. 4(A), a protective member 83 for covering the urging member 84 is provided on the upper face part 63 of the injection part 60. The protective member 83 defines a space 83a that communicates with the housing space 60a of the injection part 60 around the urging member 84. The urging member 84 is accommodated in the space 83a in a stretchably/contractibly transformable state along a stretching direction of the tube body 70. The insertion member 82 is inserted into a lumen of the urging member 84 in the space 83a.

For example, the protective member 83 may be formed of a film-like member deformable according to a pressing operation of the operation portion 81 and an expansion/contraction operation of the urging member 84. Examples of a material forming the protective member 83 may include the same material as that of the cover portion 72. Note that a shape, etc. of the protective member 83 is not particularly limited as long as the protective member 83 can form the space 83a covering a circumference of the urging member 84. For example, the space 83a may not have a shape of gradually widening toward the injection part 60 side as illustrated in the figure, and may be formed in a columnar shape disposed to cover the urging member 84.

A distal portion of the urging member 84 is secured to the upper face part 63 of the injection part 60, and a proximal portion of the urging member 84 comes into contact with an inner surface of the operation portion 81 in a state of not being secured. A distal portion of the insertion member 82 is secured to the occlusion member 85, and a proximal portion of the insertion member 82 is secured to the operation portion 81. A distal portion of the protective member 83 is secured to the upper face part 63 of the injection part 60, and a proximal portion of the protective member 83 is secured to the operation portion 81. For example, the respective members may be secured to each other using a method such as welding or adhesion depending on the quality of the material contained in each member. Note that the distal portion of the protective member 83 may be secured to the vertical wall part 62 of the injection part 60.

Next, a description will be given of examples of procedures of an operation of inflating the inflatable portion 40 by the injection part 60 and an operation of decompressing the inflatable portion 40 by the operation portion 81.

FIG. 4(A) illustrates a state before inflating the inflatable portion 40. In this state, the communication portion 72a is in a closed state, and the inner surface of the cover portion 72 is in close contact with the outer surface of the tube body 70.

As illustrated in FIG. 4(B), when the injection part 60 is pressed to send air into the tube body 70, air flows out from the lumen 70a of the tube body 70 via the hole portion 71 of the tube body 70. The air expands and transforms the cover portion 72 so that a part of the cover portion 72 is separated from the tube body 70, and forms a gap portion g between the cover portion 72 and the tube body 70. Due to the air flowing through the gap portion g, the slit forming the communication portion 72a opens, and the lumen 70a of the tube body 70 and the inflatable space 40a of the inflatable portion 40 communicate with each other. The air inflates the inflatable portion 40 by being injected into the inflatable space 40a of the inflatable portion 40.

Figure 5A:
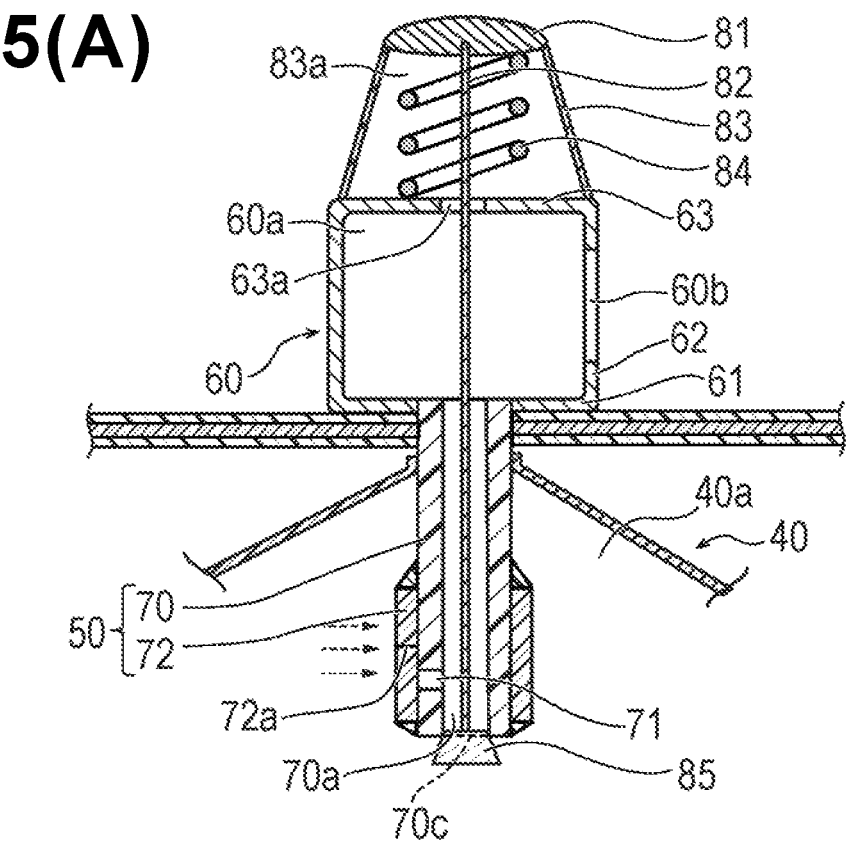
FIG. 5(A) is a cross-sectional view illustrating a state in which a communication portion is closed by gas in the inflatable portion.

As illustrated in FIG. 5(A), when pressing of the injection part 60 is released after the inflatable portion 40 is inflated, the injection part 60 is elastically transformed to return to an original shape. In this instance, when the lumen 70a of the tube body 70 becomes negative pressure with respect to the inflatable space 40a, the communication portion 72a is closed, and communication between the inflatable space 40a of the inflatable portion 40 and the housing space 60a of the injection part 60 is blocked. Further, since the inner surface of the cover portion 72 and the outer surface of the tube body 70 are in close contact with each other without any gap due to the internal pressure of the inflatable portion 40, it is possible to prevent occurrence of backflow of air from the inflatable portion 40 side to the injection part 60 side.

Figure 5B:
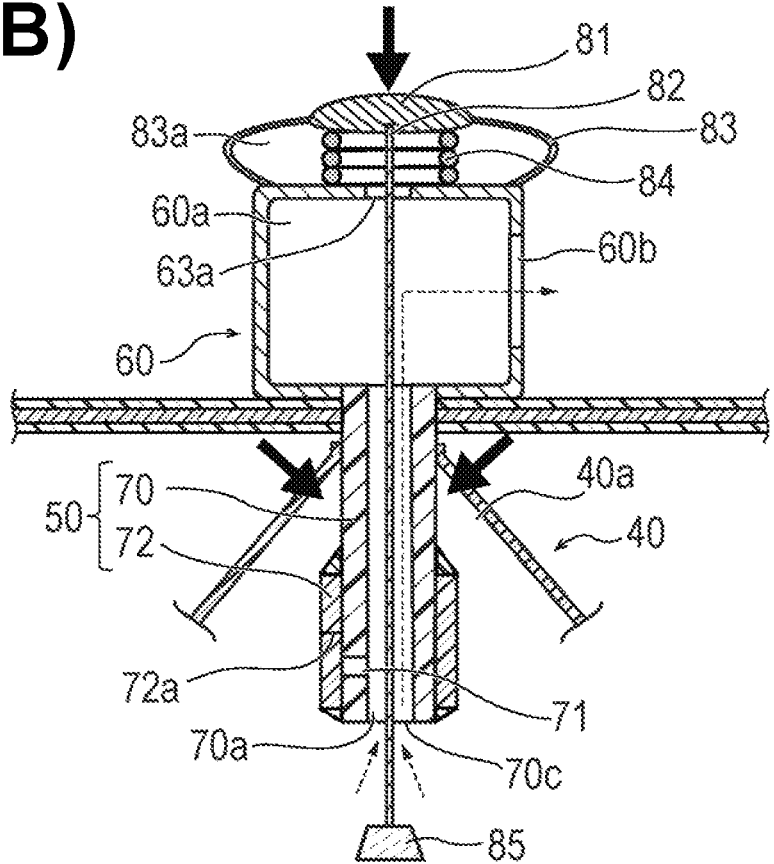
FIG. 5(B) is a cross-sectional view illustrating a state in which gas is discharged from the inflatable portion.

FIG. 5(B) illustrates a state in which the operation of decompressing the inflatable portion 40 is performed by the operation portion 81. When the inflatable portion 40 is decompressed, the operation portion 81 is pressed. When the operation portion 81 is pushed down, the occlusion member 85 is separated from the distal end opening 70c of the tube body 70, and a state in which the distal end opening 70c is sealed is released. The air previously injected into the inflatable portion 40 moves to the injection part 60 via the distal end opening 70c disposed within the inflatable portion 40. Then, the air is discharged to the outside via the hole portion 60b of the injection part 60. When decompression of the inflatable portion 40 is suspended, pressing of the operation portion 81 is released, and the occlusion member 85 is moved to the distal end opening 70c of the tube body 70 by an urging force of the urging member 84.

As described above, a structure, etc. of the hole portion 71 and the communication portion 72a can be arbitrarily set. However, to precisely control injection of air into the inflatable portion 40 and discharge of air from the inflatable portion 40, for example, it is preferable that the hole portion 71 and the communication portion 72a are formed as follows.

In a circumferential direction of the tube body 70, the hole portion 71 is preferably disposed at the same position as that of the communication portion 72a (an overlapping position in the circumferential direction). When the hole portion 71 and the communication portion 72a are disposed at overlapping positions in the circumferential direction, air can be efficiently moved from the hole portion 71 to the communication portion 72a.

In addition, it is preferable that only one communication portion 72a is provided in the tube body 70. As described above, when air is injected from the injection part 60, the cover portion 72 is inflated and transformed, and the gap portion g is formed between the outer surface of the tube body 70 and the inner surface of the cover portion 72. Since air can be efficiently sent to the communication portion 72a side through this gap portion g, it is possible to sufficiently pressurize the inflatable portion 40 using one communication portion 72a. By setting the number of communication portions 72a to one, it is also possible to prevent backflow of air from being easily caused by an increase in number (area) of the communication portions 72a.

In addition, it is preferable that the hole portion 71 is disposed close to the communication portion 72a to an extent that backflow does not occur such that the hole portion 71 does not overlap the communication portion 72a in the extending direction of the tube body 70, that is, in a cross section perpendicular to the axial center of the tube body 70 (cross section illustrated in FIG. 4(A)). As described above, since air can be moved to the communication portion 72a side through the gap portion g, there is no need to dispose the communication portion 72a in an overlapping manner in the extending direction of the tube body 70. Further, when the above-described arrangement is adopted, it is possible to prevent air from unintentionally flowing back due to inadvertent communication between the hole portion 71 and the communication portion 72a, and to efficiently move air from the hole portion 71 to the communication portion 72a.

Next, a description will be given of a use of the hemostatic device 10 according to the exemplary embodiment.

Before the hemostatic device 10 is mounted on the wrist W, as illustrated in FIG. 2, the inflatable portion 40 is in a state of not being inflated. As illustrated in FIG. 6 and FIG. 7, when the radial artery R of the right hand wrist W is punctured, the puncture site P is at a position biased to a thumb side. Normally, the introducer sheath is indwelled in the puncture site P. The band 20 is wrapped around the wrist W in which the introducer sheath is indwelled, the inflatable portion 40 and the band 20 are positioned such that the marker 40c provided on the inflatable portion 40 overlaps the puncture site P, and the male side 31 and the female side 32 of the surface fastener 30 are brought into contact with each other and joined to each other, thereby mounting the band 20 on the wrist W.

After the hemostatic device 10 is mounted on the wrist W, as illustrated in FIG. 4(B), the injection part 60 is deformed while blocking the hole portion 60b of the injection part 60 using a finger, air in the injection part 60 is injected into the inflatable portion 40, and the inflatable portion 40 and the auxiliary pressing portion 45 are inflated. Since the inflatable portion 40 can be inflated by the injection part 60 integrated with the inflatable portion 40, a doctor or a nurse may not carry a separate dedicated instrument (syringe, etc.) for inflating the inflatable portion 40.

After the inflatable portion 40 is inflated, the introducer sheath is withdrawn from the puncture site P.

It is possible to adjust the amount of air to the inflatable portion 40 and the auxiliary pressing portion 45 and adjust a pressing force applied to the puncture site P by the inflatable portion 40 by operating the operation portion 81 according to a progressing state of hemostasis and an elapsed time after withdrawing the introducer sheath. For example, when the inflated inflatable portion 40 continues to press the puncture site P and a surrounding blood vessel or nerve for a long time, there is the case of causing numbness or pain or occluding the blood vessel. In addition, in order to prevent vascular occlusion, etc., the pressing force acting on the puncture site P may be reduced over time by performing a decompression operation of discharging some air in the inflatable portion 40 over time after inflation of the inflatable portion 40 to gradually decrease the internal pressure of the inflatable portion 40. Since the decompression operation in the hemostatic device 10 can be performed by the operation portion 81, the doctor or the nurse may eliminate an effort to carry the dedicated instrument (syringe, etc.) for performing the decompression operation.

When a predetermined time elapses and hemostasis in the puncture site P is completed, the hemostatic device 10 is removed. The hemostatic device 10 is removed from the wrist W by peeling off the male side 31 and the female side 32 of the surface fastener 30. Note that the hemostatic device 10 may be removed after removing air in the inflatable portion 40 by operating the operation portion 81.

As described above, the hemostatic device 10 according to the exemplary embodiment includes the band 20 for wrapping around the puncture site P of the wrist W, the means for securing 30 that secures the band 20 in a state of being wrapped around the wrist, the inflatable portion 40 connected to the band 20 and inflated by being injected with air, the injection part 60 that can be elastically transformed and can inject air into the inflatable portion 40, and the tube body 70 that connects the inflatable space 40a of the inflatable portion 40 and the housing space 60a of the injection part 60 to each other. In addition, the tube body 70 has the hole portion 71 opening in the inflatable portion 40 and the cover portion 72 disposed on the tube body 70 to cover the hole portion 71. In addition, the cover portion 72 has the communication portion 72a capable of allowing communication between the inflatable space 40a and the housing space 60a by air discharged from the hole portion 71 when air is injected into the inflatable portion 40 from the injection part 60.

In the hemostatic device 10, when the injection part 60 is elastically transformed, air moves via the tube body 70, and the inflatable space 40a of the inflatable portion 40 and the housing space 60a of the injection part 60 communicate with each other by the communication portion 72a. The inflatable portion 40 inflates by being injected with air via the communication portion 72a. In addition, by the lumen 70a of the tube body 70 becoming negative pressure with respect to the inflatable space 40a when the injection part 60 is elastically transformed to return to the original shape, the communication portion 72a blocks communication between the inflatable space 40a of the inflatable portion 40 and the housing space 60a of the injection part 60. In this way, the hemostatic device 10 can easily and appropriately control movement of air between the inflatable portion 40 and the injection part 60 by the communication portion 72a formed in the cover portion 72. Therefore, according to the exemplary embodiment, it is possible to provide the hemostatic device capable of inflating the inflatable portion 40 by a simple operation without using a dedicated instrument separate from the hemostatic device 10.

In addition, the communication portion 72a is disposed at a different position from that of the hole portion 71 in the cross section perpendicular to the axial center of the tube body 70. For this reason, it is possible to prevent the position of the hole portion 71 and the position of the communication portion 72a from inadvertently overlapping each other so that air is unintentionally injected into the inflatable portion 40 or air is discharged from the inflatable portion 40. Further, when air is injected from the injection part 60, it is possible to form the gap portion g extending to the communication portion 72a along the axial direction of the tube body 70 between the outer surface of the tube body 70 and the inner surface of the cover portion 72, and to efficiently guide air to the communication portion 72a.

In addition, the outer surface of the tube body 70 and the inner surface of the cover portion 72 are in close contact with each other in a state in which air is not injected into the inflatable portion 40 from the injection part 60. For this reason, it is possible to increase airtightness of the inflatable portion 40 in a state in which the injection part 60 is not operated, and to prevent air from being inadvertently discharged from the inflatable portion 40.

In addition, the injection part 60 has the operation portion 81 disposed on the outer surface of the injection part 60 and the occlusion member 85 connected to the operation portion 81. The tube body 70 includes the distal end opening 70c at an end portion of the tube body 70 disposed inside the inflatable space 40a. The occlusion member 85 seals the distal end opening 70c in a state of not pressing the operation portion 81, and communicates between the distal end opening 70c and the injection part 60 in a state of pressing the operation portion 81. For this reason, it is possible to discharge air from the inflatable portion 40 by a simple operation of pressing the operation portion 81. In addition, since a mechanism for discharging air is integrated, the hemostatic device 10 does not require a dedicated instrument for discharging air. Therefore, it is possible to perform decompression of the inflatable portion 40 by a simple operation without using a dedicated instrument separate from the hemostatic device 10.

In addition, the operation portion 81 has the urging member 84 that applies an urging force in a direction in which the occlusion member 85 is pressed against the distal end opening 70c of the tube body 70. The occlusion member 85 communicates between the distal end opening 70c and the injection part 60 in a state in which the operation portion 81 is moved against an urging force of the urging member 84. In the state in which the operation portion 81 is not pressed, the urging member 84 prevents the distal end opening 70c from inadvertently communicating with the inflatable portion 40 and increases airtightness of the distal end opening 70c by pressing the occlusion member 85 against the distal end opening 70c. Further, the urging member 84 automatically moves a position of the occlusion member 85 to the distal end opening 70c by an urging force after completing the operation of pressing the operation portion 81, and thus may prevent air from being unintentionally discharged from the inflatable portion 40 after pressing the operation portion 81.

In addition, the communication portion 72a is formed as a slit opened by air discharged from the hole portion 71. For this reason, by performing an operation of elastically transforming and deforming the injection part 60, it is possible to easily open the communication portion 72a, and to efficiently inject air into the inflatable space 40a of the inflatable portion 40.

Referring to a configuration of the operation portion included in the hemostatic device 10, a specific shape, structure, etc. are not limited as long as the occlusion member 85 is moved by being pressed to allow the distal end opening 70c of the tube body 70 to be opened. For example, the operation portion may be configured as in each modification described below.

Figure 8:
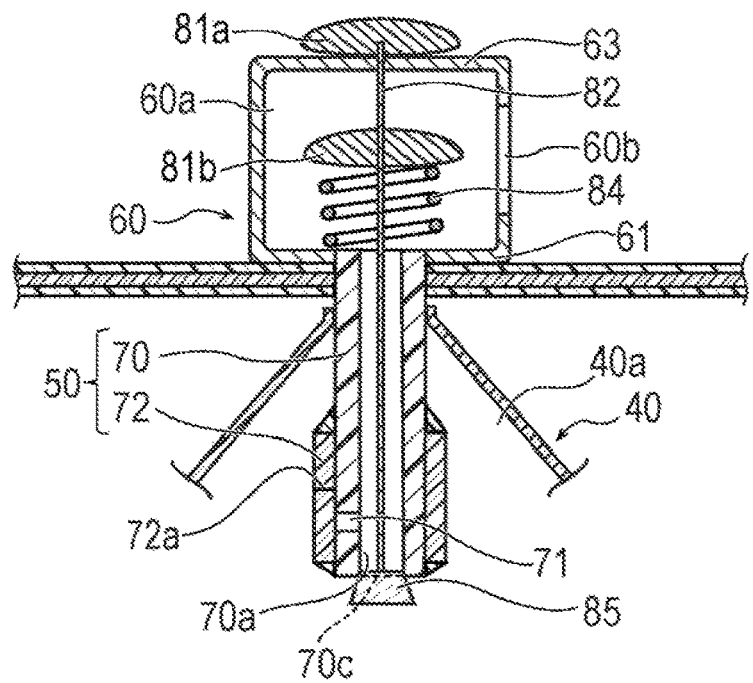
FIG. 8 is a cross-sectional view illustrating a modification of the operation portion.

As in a first modification illustrated in FIG. 8, the operation portion may include a first operation portion 81a disposed on an outer surface of the upper face part 63 of the injection part 60 and a second operation portion 81b disposed in the housing space 60a of the injection part 60. In the first modification, the second operation portion 81b is secured to the proximal portion of the urging member 84. When the first operation portion 81a is pressed from the outside of the injection part 60, the second operation portion 81b connected to the insertion member 82 moves to the distal side in the housing space 60a against an urging force of the urging member 84 to move the occlusion member 85 from the distal end opening 70c of the tube body 70. The distal end opening 70c communicates with the inflatable space 40a of the inflatable portion 40 by movement of the occlusion member 85.

Figure 9:
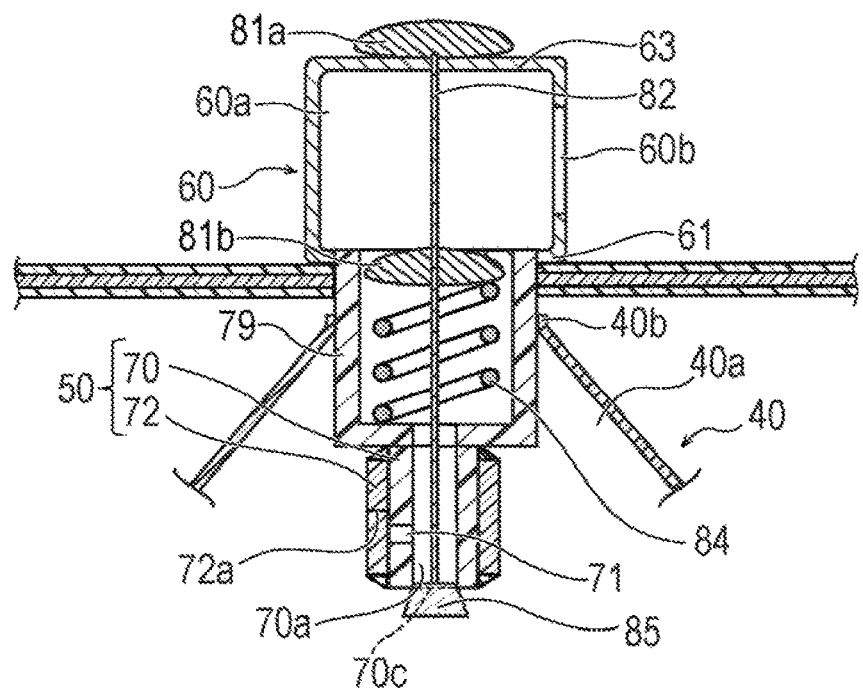
FIG. 9 is a cross-sectional view illustrating another modification of the operation portion.

In addition, as in a second modification illustrated in FIG. 9, the operation portion may include a first operation portion 81a disposed on the outer surface of the upper face part 63 of the injection part 60 and a second operation portion 81b disposed in a tubular member 79 that connects the injection part 60 and the tube body 70 to each other. In the second modification, the second operation portion 81b is secured to the proximal portion of the urging member 84. The urging member 84 is disposed in the tubular member 79. When the first operation portion 81a is pressed from the outside of the injection part 60, the second operation portion 81b connected to the insertion member 82 moves to the distal side in the tubular member 79 against an urging force of the urging member 84 to move the occlusion member 85 from the distal end opening 70c. The distal end opening 70c communicates with the inflatable space 40a of the inflatable portion 40 by movement of the occlusion member 85. Note that in the second modification, the inflatable portion 40 is connected to the tubular member 79 via the connecting portion 40b.

Figure 10A:
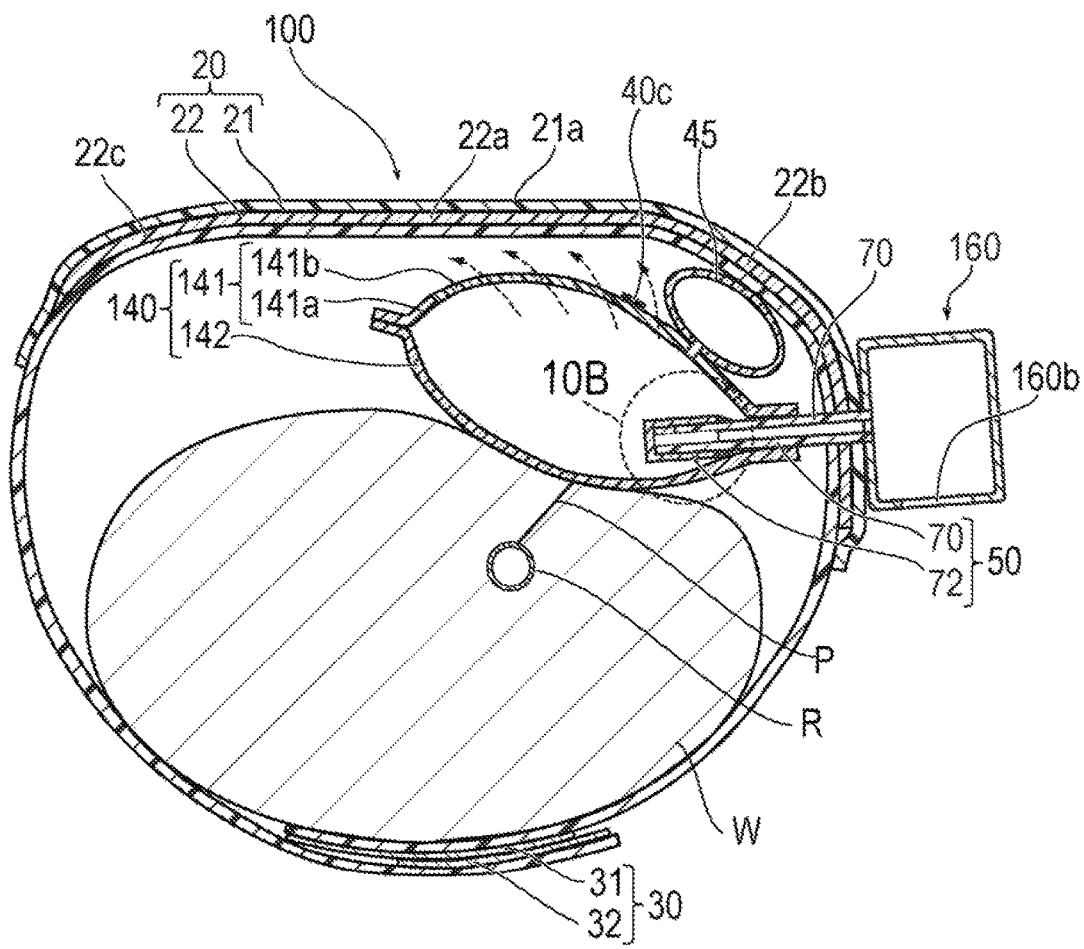
FIG. 10(A) is a cross-sectional view illustrating a hemostatic device in a state in which the hemostatic device is mounted on the wrist.
Figure 10B:
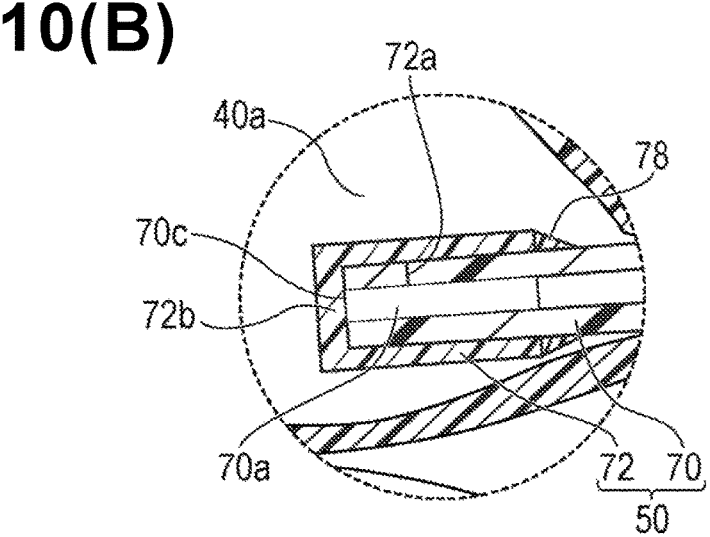
FIG. 10(B) is an enlarged view of a portion indicated by a broken line portion 10B illustrated in FIG. 10(A).

FIGS. 10(A) and 10(B) are diagrams for description of a hemostatic device 100 according to an exemplary Modification 1 embodiment. The hemostatic device 100 according to the exemplary Modification 1 embodiment will be described with reference to FIGS. 10(A) and 10(B). Note that the same reference symbol will be assigned to the same configuration as that of the embodiment, and a description thereof will be omitted.

The hemostatic device 100 according to the Modification 1 embodiment is different from the embodiment in that an inflatable portion 140 functions as a discharge unit that discharges air in the inflatable portion 140. In addition, the hemostatic device 100 does not include a mechanism (the operation portion 81, the urging member 84, the occlusion member 85, etc.) for operating discharge of air from the inflatable portion 140.

As illustrated in FIG. 10(A), the inflatable portion 140 is formed by superposing a first sheet 141 and a second sheet 142 on one another to form a bag shape.

The first sheet 141 includes a peripheral part 141a made of a thermoplastic material and a central part 141b made of a thermosetting elastomer. Note that even though the thermosetting elastomer is provided at a central portion of a surface of the inflatable portion 140 on the band 20 side in the present modification, the thermosetting elastomer may be provided at a central portion of a surface of the inflatable portion 140 on the wrist W side.

In the Modification 1 embodiment, the first sheet 141 is formed by pouring the thermoplastic material and the thermosetting elastomer into predetermined positions of a mold having a predetermined shape, respectively, and integrally molding the thermoplastic material and the thermosetting elastomer. However, the first sheet 141 may be formed by disposing a rectangular member (corresponding to the "central part 141b") made of a thermosetting elastomer at a center of a frame-shaped member (corresponding to the "peripheral part 141a") made of a thermoplastic material and bonding the members using and adhesive.

The second sheet 142 is made of a thermoplastic material.

A portion where the peripheral part 141a of the first sheet 141 and a peripheral part of the second sheet 142 overlap each other is welded.

One side of the peripheral part 141a of the first sheet 141 and one side of the peripheral part of the second sheet 142 are welded with the tube body 70 interposed therebetween. The inflatable portion 140 is connected to the band 20 on which the tube body 70 is disposed by this welding.

The thermoplastic material used for the inflatable portion 140 is not particularly limited. However, for example, it is possible to use a thermoplastic resin such as polyvinyl chloride, polyethylene, polypropylene, or polyvinylidene chloride or various thermoplastic elastomers such as an olefinic thermoplastic elastomer, a styrene thermoplastic elastomer, and a polyethylene thermoplastic elastomer.

A material having higher gas permeability than that of the thermoplastic material used for the inflatable portion 140 is used as the thermosetting elastomer used for the inflatable portion 140. As such a material, for example, it is possible to use silicone, natural rubber, etc. For this reason, after inflation of the inflatable portion 140, while the inflatable portion 140 applies a pressing force to the puncture site P through a region made of the thermosetting elastomer of the inflatable portion 140, gas in the inflatable portion 140 escapes to the outside of the inflatable portion 140 over time (indicated by a dotted arrow in FIG. 10(A)).

As illustrated in FIG. 10(B), the cover portion 72 has a bottom face part 72b that covers the distal end opening 70c of the tube body 70. In addition, the proximal portion of the cover portion 72 is secured to the tube body 70 in a state of sealing a gap between the proximal portion and the outer surface of the tube body 70. The cover portion 72 and the tube body 70 are secured by the adhesive 78. However, for example, securing may be performed by welding.

The injection part 160 has the hole portion 160b blocked with the finger, etc. when air is injected into the inflatable space 140a of the inflatable portion 140. The injection part 160 has substantially the same configuration as that of the injection part 60 (see FIG. 4(A)) according to the exemplary embodiment except that the mechanism (the operation portion 81, the urging member 84, and the occlusion member 85) for operating discharge of air from the inflatable portion 140 is not provided.

As described above, according to the hemostatic device 100 according to the Modification 1 embodiment, air in the inflatable portion 140 escapes to the outside of the inflatable portion 140 over time through the region made of the thermosetting elastomer of the inflatable portion 140. For this reason, even when the doctor or the nurse does not perform the decompression operation, it is possible to reduce a pressing force acting on the puncture site P over time while applying the pressing force to the puncture site P. For this reason, it is possible to reduce a burden of treatment and personnel expenses of the doctor or the nurse.

Figure 11:
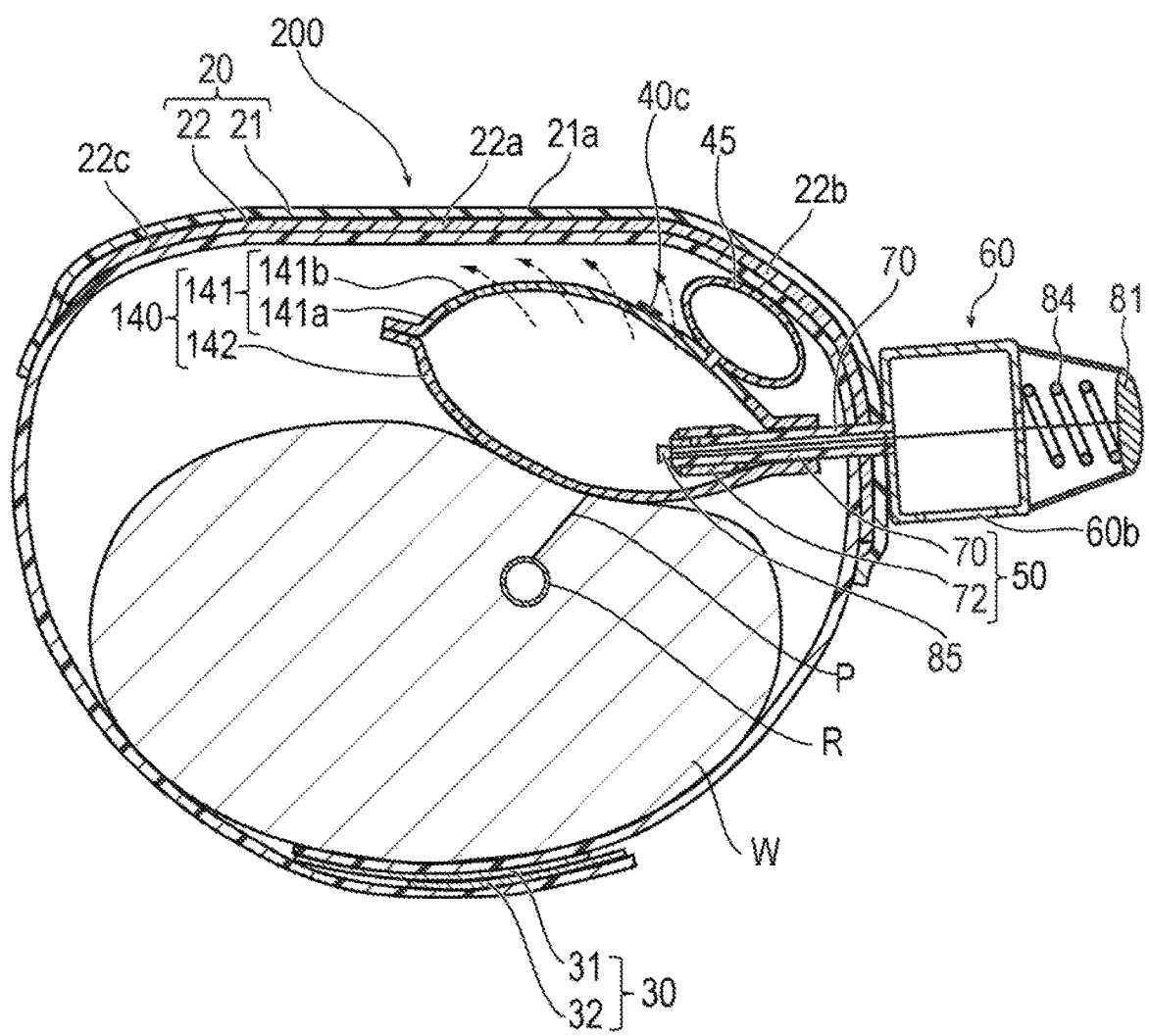
FIG. 11 is a cross-sectional view illustrating a state in which a hemostatic device according to Modification 2 is mounted on the wrist.

FIG. 11 is a diagram for description of a hemostatic device 200 according to a Modification 2 embodiment. The hemostatic device 200 according to Modification 2 will be described with reference to FIG. 11. Note that the same reference symbol will be assigned to the same configuration as that of the exemplary embodiment and the Modification 1 embodiment, and a description thereof will be omitted.

In the hemostatic device 200 according to the Modification 2 embodiment, a structure of the inflatable portion 140 is configured similarly to the hemostatic device 100 according to the Modification 1 embodiment. Further, the hemostatic device 200 has the mechanism (the operation portion 81, the urging member 84, and the occlusion member 85) for operating discharge of air from the inflatable portion 140. A structure of an injection part 60 of the hemostatic device 200 is configured similarly to the injection part 60 according to the embodiment (see FIG. 4(A)).

In the hemostatic device 200 according to Modification 2, similarly to the hemostatic device 100 according to Modification 1, air in the inflatable portion 140 escapes to the outside of the inflatable portion 140 over time through the region made of the thermosetting elastomer of the inflatable portion 140. For this reason, even when the doctor or the nurse does not perform the decompression operation, it is possible to reduce a pressing force acting on the puncture site P over time while applying the pressing force to the puncture site P.

Further, since the hemostatic device 200 has the mechanism (the operation portion 81, the urging member 84, and the occlusion member 85) for operating discharge of air from the inflatable portion 140, it is possible to discharge air from the inflatable portion 140 at any arbitrary time by operating the operation portion 81. For example, with only an automatic decompression mechanism for discharging air through the region made of the thermosetting elastomer of the inflatable portion 140, in a case in which air is excessively injected into the inflatable portion 140, there is a possibility that a desired amount of air may not be immediately discharged from the inflatable portion 140, and the radial artery R or a nerve may be excessively pressed. The hemostatic device 200 may appropriately adjust the pressing force of the inflatable portion 140 by operating the operation portion 81, and thus it is possible to prevent the above-mentioned problem from occurring.

Even though the hemostatic device according to the disclosure herein has been described above through the exemplary embodiment and modifications thereto, the disclosure is not limited only to the respective configurations described above, and can be appropriately changed based on the description of claims.

For example, each portion included in the hemostatic device may be replaced with a portion having an arbitrary configuration capable of exerting the same function. In addition, an arbitrary component may be added.

In addition, the disclosure is not limited to the hemostatic device used by being mounted on the wrist, and may be applied to a hemostatic device used by being mounted on a leg, etc.

In addition, even though a case in which the hemostatic device includes the auxiliary pressing portion has been described in the exemplary embodiment, the auxiliary pressing portion may not be included.

In addition, in the exemplary embodiment, an example in which discharge of air in the inflatable portion can be controlled by the operation portion and the occlusion member has been described. However, for example, the hemostatic device may not include the operation portion and the occlusion member, and gas such as air may be discharged by a dedicated instrument separate from the hemostatic device. In addition, an example in which the urging member is included as a specific structure of the operation portion has been given. However, a configuration of the operation portion is not limited as long as the operation portion has a structure in which the occlusion member is moved by a pressing operation so that the inflatable portion and the lumen of the tube body communicate with each other.

The detailed description above describes embodiments and modifications of a hemostatic device and method representing examples of the inventive hemostatic device and method disclosed here. The invention is not limited, however, to the precise embodiments and modifications described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
a band adapted to be wrapped around a limb of a patient at a site on the limb where bleeding is to be stopped;
securing means for securing the band to the limb in a wrapped state;
an inflatable portion connected to the band and adapted to be inflated by injecting gas;
an injection part which is adapted to inject gas into the inflatable portion; and
a tube body adapted to connect a lumen of the inflatable portion and a lumen of the injection part,
wherein the tube body has a hole portion opening into the inflatable portion and a cover portion disposed on the tube body and configured to cover the hole portion,
wherein the cover portion has a communication portion that allows communication between the lumen of the inflatable portion and the lumen of the injection part by gas discharged from the hole portion when gas is injected into the inflatable portion from the injection part, and
wherein an outer surface of the tube body and a portion of an inner surface of the cover portion are in contact with each other in a state in which gas is not injected into the inflatable portion from the injection part, and are not in contact with each other in a state in which gas is injected into the inflatable portion from the injection part.

2. The hemostatic device according to claim 1, wherein the communication portion is disposed at a different position from a position of the hole portion in a cross section perpendicular to an axial center of the tube body.

3. The hemostatic device according to claim 1,
wherein the injection part has an operation portion disposed on an outer surface of the injection part and an occlusion member connected to the operation portion, and the tube body includes an end opening at an end portion of the tube body disposed in the lumen of the inflatable portion, and
wherein the occlusion member is configured to seal the end opening in a state of not pressing the operation portion, and to allow communication between the end opening and the injection part in a state of pressing the operation portion.

4. The hemostatic device according to claim 3,
wherein the operation portion further has an urging member configured to apply an urging force in a direction in which the occlusion member is pressed against the end opening, and
wherein the occlusion member is configured to allow communication between the end opening and the injection part in a state in which the operation portion is moved against the urging force.

5. The hemostatic device according to claim 1, wherein the communication portion corresponds to a slit configured to open by virtue of gas discharged from the hole portion.

6. The hemostatic device according to claim 1, wherein the inflatable portion has gas permeability to discharge gas in the lumen of the inflatable portion to an outside over time in a state of inflating the inflatable portion.

7. A hemostatic device comprising:
a flexible band configured to be wrapped around a hemostasis-requiring site of a limb;
a securing portion that secures the band in a state where the band is wrapped around the limb;
an inflatable portion configured to overlap with the band and inflate when a fluid is injected into the inflatable portion;
an injection part configured to inject gas into the inflatable portion; and
a backflow check structure including a tube body and a cover portion;
wherein the tube body connects an interior of the inflatable portion and an interior of the injection part;
wherein the tube body includes a hole portion opening into the interior of the inflatable portion and the cover portion is disposed over the tube body so as to cover the hole portion and be in contact with the tube body,
wherein the cover portion includes a communication portion adapted to have an open state when gas is injected into the inflatable portion from the injection part thereby allowing communication between the interior of the inflatable portion and the interior of the injection part and to have a closed state so as to prevent gas from being inadvertently discharged from the inflatable portion,
wherein the injection part includes an operation portion disposed on an outer surface of the injection part and an occlusion member connected to the operation portion, and
wherein the occlusion member is connected to the operation portion by an insertion member extending through the tube body such that the occlusion member is configured to seal a distal end opening of the tube body when the operation portion is pressed.

8. The hemostatic device according to claim 7, wherein the injection part includes a hole allowing gas to be taken into the interior of the injection part.

9. The hemostatic device according to claim 7, wherein the communication portion comprises a slit penetrating the cover portion in a thickness direction.

10. The hemostatic device according to claim 7, wherein the operation member further comprises an urging member adapted to apply a force for pressing the occlusion member against the distal end opening of the tube body.

11. The hemostatic device according to claim 10, wherein the urging member comprises a coil spring.

12. The hemostatic device according to claim 10, wherein the operation portion defines a first operation portion and further comprising a second operation portion.

13. The hemostatic device according to claim 7, wherein the inflatable portion includes at least a portion made from a thermosetting elastomer, whereby gas in the inflatable portion escapes to an outside of the inflatable portion over time.

* * * * *